United States Patent [19]

Feige et al.

[11] Patent Number: 5,229,405
[45] Date of Patent: Jul. 20, 1993

[54] USE OF 2-IMINOTHIAZOLIDIN-4-ONE DERIVATIVES AS NOVEL PHARMACEUTICAL ACTIVE INGREDIENTS

[75] Inventors: Ulrich Feige, Riehen; Irmgard Wiesenberg, Weil am Rhein; Leo Widler, Münchenstein; Pier G. Ferrini, Binningen; Martin Missbach, Rheinfelden, all of Switzerland

[73] Assignee: Ciba-Geigy Corporation, Ardsley, N.Y.

[21] Appl. No.: 866,926

[22] Filed: Apr. 10, 1992

[30] Foreign Application Priority Data

Apr. 12, 1991 [CH] Switzerland ............. 1087/91

[51] Int. Cl.$^5$ ..................... A61K 31/425
[52] U.S. Cl. ..................... 514/369
[58] Field of Search ..................... 514/369

[56] References Cited

U.S. PATENT DOCUMENTS

| | | | |
|---|---|---|---|
| 4,489,069 | 12/1984 | Storni | 548/117 |
| 4,582,841 | 4/1986 | Storni | 514/369 |
| 4,697,020 | 9/1987 | Storni et al. | 548/184 |

FOREIGN PATENT DOCUMENTS

| | | |
|---|---|---|
| 22515 | 1/1981 | European Pat. Off. |
| 85275 | 8/1983 | European Pat. Off. |
| 2035414 | 1/1971 | Fed. Rep. of Germany |
| 2632745 | 2/1977 | Fed. Rep. of Germany |
| 2632746 | 2/1977 | Fed. Rep. of Germany |
| 2632747 | 2/1977 | Fed. Rep. of Germany |
| 511877 | 10/1971 | Switzerland |
| 594648 | 1/1978 | Switzerland |

*Primary Examiner*—S. J. Friedman
*Attorney, Agent, or Firm*—Irving M. Fishman; Karen G. Kaiser

[57] ABSTRACT

Compounds of the formula I

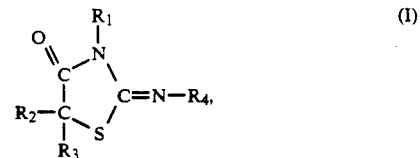

in which $R_1$ is lower alk-2-en-1-yl, lower alk-3-en-2-yl, lower alk-2-yn-1-yl or lower alkyl substituted in the 2,3-position by radicals which can be eliminated to give a double bond, $R_2$ is hydrogen and $R_3$ is methyl which is unsubstituted or substituted by radicals which can be eliminated together with hydrogen $R_2$ to give a double bond or $R_2$ and $R_3$ are both hydrogen or lower alkyl or are together methylene and $R_4$ is a group of the formula Ia, Ib or Ic

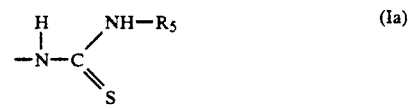

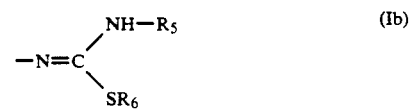

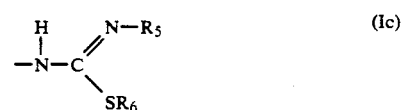

in which $R_5$ is hydrogen, lower alkyl, lower alk-2-en-1-yl or lower alk-2-yn-1-yl and $R_6$ is a group of the formula Id or Ie

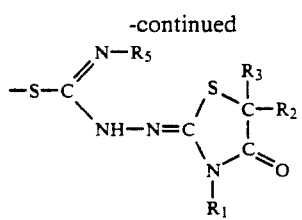 (Ie)
in which $R_1$, $R_2$, $R_3$ and $R_5$ are as defined, and their pharmaceutically acceptable salts can be used in a novel manner for the treatment of diseases of the rheumatoid type.
11 Claims, No Drawings

USE OF 2-IMINOTHIAZOLIDIN-4-ONE DERIVATIVES AS NOVEL PHARMACEUTICAL ACTIVE INGREDIENTS

The invention relates to the use of 2-iminothiazolidin-4-one derivatives of the formula I

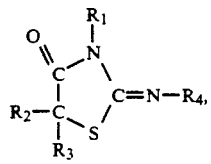

in which $R_1$ is lower alk-2-en-1-yl, lower alk-3-en-2-yl, lower alk-2-yn-1-yl or lower alkyl substituted in the 2,3-position by radicals which can be eliminated to give a double bond, $R_2$ is hydrogen and $R_3$ is methyl which is unsubstituted or substituted by radicals which can be eliminated together with hydrogen $R_2$ to give a double bond or $R_2$ and $R_3$ are both hydrogen or lower alkyl or are together methylene and $R_4$ is a group of the formula Ia, Ib or Ic

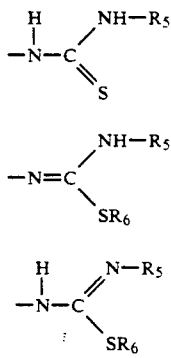

in which $R_5$ is hydrogen, lower alkyl, lower alk-2-en-1-yl or lower alk-2-yn-1-yl and $R_6$ is a group of the formula Id or Ie

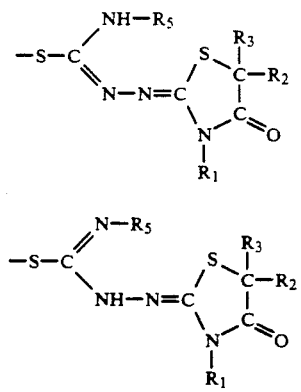

in which $R_1$, $R_2$, $R_3$ and $R_5$ are as defined, and their pharmaceutically acceptable salts for the treatment of diseases of the rheumatoid type or for the production of pharmaceutical preparations intended for this purpose, a method for the treatment of diseases of the rheumatoid type and pharmaceutical preparations intended for this purpose, comprising a compound of the formula I or a pharmaceutically acceptable salt thereof in addition to customary pharmaceutical adjuncts.

Lower alkyl substituted in the 2,3-position by radicals which can be eliminated to give a double bond is, for example, 2- or 3-amino-, 2- or 3-lower alkylamino-or 2- or 3-di-lower alkylamino-lower alkyl, 2- or 3-lower alkyleneamino-, 2- or 3-(aza)lower alkyleneamino-, 2- or 3-(oxa)lower alkyleneamino-or 2- or 3-(thia)lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl or 2- or 3-halo-lower alkyl.

Methyl substituted by radicals which can be eliminated together with hydrogen $R_2$ to give a double bond is, for example, di-lower alkylaminomethyl or halomethyl.

Above and below, lower radicals and compounds, for example, are to be understood as meaning those having not more than 7, prepferably having not more than 4, carbon atoms (C atoms).

Lower alkyl is, for example, $C_1$–$C_7$alkyl, preferably $C_1$–$C_4$alkyl, such as, in particular, methyl or secondarily ethyl, propyl, isopropyl or butyl, but can also be isobutyl, secondary butyl, tertiary butyl or a $C_5$–$C_7$alkyl group, such as a pentyl, hexyl or heptyl group.

Lower alkoxy is, for example, $C_1$–$C_7$alkoxy, preferably $C_1$–$C_4$alkoxy, such as methoxy, ethoxy, propoxy, isopropoxy or butoxy, but can also be isobutoxy, secondary butoxy, tertiary butoxy or a pentyloxy, hexyloxy or heptyloxy group.

Lower alk-2-en-1-yl is, for example, $C_3$–$C_7$alk-2-en-1-yl, in particular $C_3$–$C_5$alk-2-en-1-yl, such as allyl (prop-2-en-1-yl) or methallyl (2-methylprop-2-en-1-yl).

Lower alk-3-en-2-yl is, for example, $C_3$–$C_7$alk-3-en-2-yl, in particular $C_3$–$C_5$alk-3-en-2-yl, such as but-3-en-2-yl.

2- or 3-amino-lower alkyl is, for example, 2-amino-$C_3$–$C_7$alkyl, in particular amino-$C_3$–$C_5$alkyl, such as 2-aminopropyl or 2-amino-2-methylpropyl, or 3-amino-$C_3$–$C_7$alkyl, in particular 3-amino-$C_3$–$C_5$alkyl, such as 3-aminopropyl or 3-amino-2-methylpropyl.

2- or 3-lower alkylamino-lower alkyl is, for example, 2-$C_1$–$C_4$alkylamino-$C_3$–$C_7$alkyl, in particular $C_1$–$C_4$alkylamino-$C_3$–$C_5$alkyl, such as 2-$C_1$–$C_4$alkylaminopropyl or 2-$C_1$–$C_4$alkylamino-2-methylpropyl or 3-$C_1$–$C_4$alkylamino-$C_3$–$C_7$alkyl, in particular 3-$C_1$–$C_4$alkylamino-$C_3$–$C_5$alkyl, such as 3-$C_1$–$C_4$alkylaminopropyl or 3-$C_1$–$C_4$alkylamino-2-methylpropyl, where $C_1$–$C_4$alkyl is, for example, methyl, ethyl, propyl or butyl.

Di-lower alkylaminomethyl is, for example, N,N-di-$C_1$–$C_4$alkylaminomethyl, such as N,N-dimethylaminomethyl, N,N-diethylaminomethyl, N-ethyl-N-methylaminomethyl, N,N-dipropylaminomethyl, N-methyl-N-propylaminomethyl, N-isopropyl-N-methylaminomethyl or N-butyl-N-methylaminomethyl, but can also be N-isobutyl-N-methylaminomethyl, N-methyl-N-secondary butylaminomethyl, N-methyl-N-tertiary butylaminomethyl or an N-methyl-N-pentylaminomethyl, N-hexyl-N-methylaminomethyl or N-heptyl-N-methylaminomethyl group.

2- or 3- di-lower alkylamino-lower alkyl is, for example, 2-(N,N-di-$C_1$–$C_4$alkylamino)-$C_3$–$C_7$alkyl, in particular 2-(N,N-di-$C_1$–$C_4$alkylamino)-$C_3$–$C_5$alkyl, such as 2-(N,N-di-$C_1$–$C_4$alkylamino)propyl or 2-(N,N-di-$C_1$-$C_4$alkylamino)-2-methylpropyl or 3-(N,N-di-$C_1$–$C_4$alkylamino)-$C_3$–$C_7$alkyl, in particular 3-(N,N-di-$C_1$–$C_4$alkylamino)-$C_3$–$C_5$alkyl, such as 3-(N,N-di-$C_1$–$C_4$alkylamino)propyl or 3-(N,N-di-$C_1$-$C_4$alkylamino)-2- methylpropyl, where $C_1$–$C_4$alkyl is, for example, methyl, ethyl, propyl or butyl.

2- or 3-lower alkyleneamino-lower alkyl is, for example, 4- to 7-membered 2-(N,N-alkyleneamino)-$C_3$–$C_7$alkyl, in particular 2-(N,N-alkyleneamino)-$C_3$–$C_5$alkyl, such as 2-(N,N-alkyleneamino)propyl or 2-(N,N-alkyleneamino)-2-methylpropyl or 3-(N,N-alkyleneamino)-$C_3$–$C_7$alkyl, in particular 3-(N,N-alkyleneamino)-$C_3$–$C_5$alkyl, such as 3-(N,N-alkyleneamino)propyl or 3-(N,N-alkyleneamino)-2-methylpropyl, where 4- to 7-membered N,N-alkyleneamino is in particular pyrrolidino, piperidino or secondarily hexahydroazepino or octahydroazocino.

2- or 3-(aza)lower alkyleneamino-lower alkyl is, for example, 4- to 7-membered 2-[N,N-(aza)alkyleneamino]-$C_3$–$C_7$alkyl, in particular 2-[N,N-(aza)alkyleneamino]-$C_3$–$C_5$alkyl, such as 2-[N,N-(aza)alkyleneamino]propyl or 2-[N,N-(aza)alkyleneamino]-2-methylpropyl or 3-[N,N-(aza)alkyleneamino]-$C_3$–$C_7$alkyl, in particular 3-[N,N-(aza)alkyleneamino]-$C_3$–$C_5$alkyl, such as 3-[N,N-(aza)alkyleneamino]propyl or 3-[N,N-(aza)alkyleneamino]-2-methylpropyl, where 4- to 7-membered N,N-(aza)alkyleneamino is in particular piperazino or N'-$C_1$–$C_4$alkyl, such as N'-methylpiperazino, or N'-$C_1$–$C_7$alkanoylpiperazino, such as N'-acetyl- or N'-pivaloylpiperazino.

2- or 3-(oxa)lower alkyleneamino-lower alkyl is, for example, 4- to 7-membered 2-[N,N-(oxa)alkyleneamino]-$C_3$–$C_7$alkyl, in particular 2-[N,N-(oxa)alkyleneamino]-$C_3$–$C_5$alkyl, such as 2-[N,N-(oxa)alkyleneamino]propyl or 2-[N,N-(oxa)alkyleneamino]-2-methylpropyl or 3-[N,N-(oxa)alkyleneamino]-$C_3$–$C_7$alkyl, in particular 3-[N,N-(oxa)alkyleneamino]-$C_3$–$C_5$alkyl, such as 3-[N,N-(oxa)alkyleneamino]propyl or 3-[N,N-(oxa)alkyleneamino]-2-methylpropyl, where 4- to 7-membered N,N-(oxa)alkyleneamino, is in particular morpholino. 2- or 3-(thia)lower alkyleneamino-lower alkyl is, for example, 4- to 7-membered 2-[N,N-(thia)alkyleneamino]-$C_3$–$C_7$alkyl which may be S-oxidised, in particular 2-[N,N-(thia)alkyleneamino]-$C_3$–$C_5$alkyl, such as 2-[N,N-(thia)alkyleneamino]propyl or 2-[N,N-(thia)alkyleneamino]-2-methylpropyl or 3-[N,N-(thia)alkyleneamino]-$C_3$–$C_7$alkyl, in particular 3-[N,N-(thia)alkyleneamino]-$C_3$–$C_5$alkyl, such as 3-[N,N-(thia)alkyleneamino]propyl or 3-[N,N-(thia)alkyleneamino]-2-methylpropyl, where 4- to 7-membered N,N-(thia)alkyleneamino which may be S-oxidised is in particular thiomorpholino or S-oxy- or S,S-dioxythiomorpholino respectively.

2- or 3-hydroxy-lower alkyl is, for example, 2-hydroxy-$C_3$–$C_7$alkyl, in particular hydroxy-$C_3$–$C_5$alkyl, such as 2-hydroxypropyl or 2-hydroxy-2-methylpropyl, or 3-hydroxy-$C_3$–$C_7$alkyl, in particular 3-hydroxy-$C_3$–$C_5$alkyl, such as 3-hydroxypropyl or 3-hydroxy-2-methylpropyl.

2- or 3-lower alkanoyloxy-lower alkyl is, for example, 2-($C_1$–$C_7$alkanoyloxy)-$C_3$–$C_7$alkyl, in particular ($C_1$–$C_7$alkanoyloxy)-$C_3$–$C_5$alkyl, such as 2-($C_1$–$C_7$alkanoyloxy)propyl or 2-($C_1$–$C_7$alkanoyloxy)-2-methylpropyl, or 3-($C_1$–$C_7$alkanoyloxy)-$C_3$–$C_7$alkyl, in particular 3-($C_1$–$C_7$alkanoyloxy)-$C_3$–$C_5$alkyl, such as 3-($C_1$–$C_7$alkanoyloxy)propyl or 3-($C_1$–$C_7$alkanoyloxy)-2-methylpropyl, where $C_1$–$C_7$alkanoyloxy is in particular $C_1$–$C_4$alkanoyloxy, such as acetyloxy or pivaloyloxy.

2- or 3-lower alkoxycarbonyloxy-lower alkyl is, for example, 2-($C_1$–$C_7$alkoxycarbonyloxy)-$C_3$–$C_7$alkyl, in particular ($C_1$–$C_7$alkoxycarbonyloxy)-$C_3$–$C_5$alkyl, such as 2-($C_1$–$C_7$alkoxycarbonyloxy)propyl or 2-($C_1$–$C_7$alkoxycarbonyloxy)-2-methylpropyl, or 3-($C_1$–$C_7$alkoxycarbonyloxy)-$C_3$–$C_7$alkyl, in particular 3-($C_1$–$C_7$alkoxycarbonyloxy)-$C_3$–$C_5$-alkyl, such as 3-($C_1$–$C_7$alkoxycarbonyloxy)propyl or 3-($C_1$–$C_7$alkoxycarbonyloxy)-2-methylpropyl, where $C_1$–$C_7$alkoxycarbonyloxy is in particular $C_1$–$C_4$alkoxycarbonyloxy, such as tertiary butoxycarbonyloxy.

2- or 3-tri-lower alkylsilyloxy-lower alkyl is, for example, 2-(tri-$C_1$–$C_7$alkylsilyloxy)-$C_3$–$C_7$alkyl, in particular (tri-$C_1$–$C_7$alkylsilyloxy)-$C_3$–$C_5$alkyl, such as 2-(tri-$C_1$–$C_7$alkylsilyloxy)propyl or 2-(tri-$C_1$–$C_7$alkylsilyloxy)-2-methylpropyl, or 3-(tri-$C_1$–$C_7$alkylsilyloxy)-$C_3$–$C_7$alkyl, in particular 3-(tri-$C_1$–$C_7$-alkylsilyloxy)-$C_3$–$C_5$alkyl, such as 3-(tri-$C_1$–$C_7$alkylsilyloxy)propyl or 3-(tri-$C_1$–$C_7$alkylsilyloxy)-2-methylpropyl, where tri-$C_1$–$C_7$alkylsilyloxy is in particular tri-$C_1$–$C_4$-alkylsilyloxy, such as trimethylsilyloxy or tributylsilyloxy, or $C_4$–$C_7$-alkyl(di-$C_1$–$C_4$alkyl)silyloxy, such as 1,2,2-trimethylpropyl(dimethyl)silyloxy.

Halogen is, for example, halogen of atomic number of not more than 35, such as chlorine or fluorine, and additionally bromine.

2- or 3-halo-lower alkyl is, for example, 2-halo-$C_3$–$C_7$-alkyl, in particular halo-$C_3$–$C_5$alkyl, such as 2-halopropyl or 2-halo-2-methylpropyl or 3-halo-$C_3$–$C_7$alkyl, in particular 3-halo-$C_3$–$C_5$alkyl, such as 3-halopropyl or 3-halo-2-methylpropyl, where $C_1$–$C_4$alkyl is, for example, halogen of atomic number up to and including 35, such as chlorine or fluorine, and additionally bromine.

Halomethyl is, for example, halomethyl, in which halo has an atomic number of not more than 35 and is, for example, chlorine or fluorine, and additionally bromine.

The compounds of the formula I are basic and can form acid addition salts. Pharmaceutically acceptable acid addition salts of compounds of the formula I are, for example, their pharmaceutically acceptable salts with suitable mineral acids, such as halohydric acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluenesulfonates or N-cyclohexylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, maleates, fumarates, tartrates or citrates.

The compounds of the formula I and processes for their preparation based on methods known per se are known and are described, for example, in GB-1 325 061, U.S. Pat. No. 4,697,020, DE-2 405 395, DE-2 632 745, DE-2 632 746, DE-2 632 747, CH-594648, EP-085 275 and EP 22 515 as intermediates for the preparation of antitumour pharmaceutical active ingredients. Novel compounds of the formula I and their pharmaceutically acceptable salts can be prepared in an analogous manner as described therein. It is additionally known, for example from DE-2 405 395 and CH-511 877, that compounds of the formula I in which $R_1$ is methyl or lower alk-2-en-1-yl, $R_2$ is hydrogen, $R_3$ is methyl, $R_4$ is a group of the formula Ia or Id and $R_5$ is lower alk-2-en-1-yl, in turn have antitumour properties and are in particular suitable for the treatment of neoplastic diseases in warm-blooded animals. The compound of the formula I in which $R_1$ is allyl, $R_2$ is hydrogen, $R_3$ is methyl, $R_4$ is a group of the formula Ia and $R_5$ is allyl was additionally ascribed immunosuppressive effects which were not specified in greater detail in CH-511 877 and BE-753 532, on the basis of which this compound should be suitable for improving the survivability of transplanted organs and for the treatment of autoimmune diseases.

The present invention is based on the surprising finding that the compounds of the formula I and their pharmaceutically acceptable salts have, additionally to their known antitumour action which is usually in the daily dose range from about 10 to about 250 mg/kg i.p., pronounced antiarthritic properties, even at a very low dose which still does not inhibit tumours. These properties can be demonstrated in vivo, for example, in the rat adjuvant arthritis model according to I. Wiesenberg et al. Clin. Exp. Immunol. 78, 245 (1989) in the dose range from about 0.1 to about 0.3 mg/kg p.o. or i.p.

The mechanism of the antiarthritic action of the compounds of the formula I and their pharmaceutically acceptable salts is currently still not exactly known. However, it can be ruled out that a direct immunosuppressive mechanism exists via limphocytotoxicity or myelosuppression, since even doses which are more than 100 times higher than the antiarthritic dose do not lead to the otherwise to be expected massive suppression of the lymphatic organs (thymus, spleen) or to leukopenia. In the therapy of rheumatoid diseases with immunosuppresive cytostatics, for example cyclophosphamide, lymphocytotoxicity and myelosuppression are known undesired side effects.

On the other hand, it was possible to demonstrate that the compounds of the formula I and their pharmaceutically acceptable salts inhibit the synthesis of the cytokine interleukin-1 in human monocytes. Interleukin-1 is an inflammatory mediator which plays a key role in acute and chronic inflammatory processes. It is therefore to be assumed that the compounds of the formula I and their pharmaceutically acceptable salts have properties which cause the antiarthritic effects in doses which are lower than the cytostatically active dose. A causal relationship with the inhibition of cytokine synthesis mentioned could exist, although other, still unknown immunomodulatory mechanisms also cannot be excluded.

The compounds of the formula I and their pharmaceutically acceptable salts can therefore be employed for the treatment of diseases of the rheumatoid type in the sense of the "preliminary proposal of the Glossary Committee of the American Rheumatism Association". These include in particular rheumatoid arthritis, juvenile arthritis, ankylosing spondylitis and other seronegative spondylarthritises, for example arthritis in ulcerative colitis and Crohn's disease, but also reactive arthritises, collagen diseases such as Lupus erythematosus, degenerative rheumatic diseases, and extra-articular rheumatic and pararheumatic diseases, for example gout and osteoporosis.

The invention relates primarily to the use of compounds of the formula I in which $R_1$ is lower alk-2-en-1-yl, lower alk-3-en-2-yl, lower alk-2-yn-1-yl, 2- or 3-amino-, 2- or 3-lower alkylamino- or 2- or 3-di-lower alkylamino-lower alkyl, 2- or 3-lower alkyleneamino-, 2- or 3-(aza)lower alkyleneamino-, 2- or 3-(oxa)lower alkyleneamino- or 2- or 3-(thia)lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl or 2- or 3-halo-lower alkyl, $R_2$ is hydrogen and $R_3$ is di-lower alkylamino-lower alkyl or halomethyl or $R_2$ and $R_3$, independently of one another, are hydrogen or lower alkyl or together are methylene, $R_4$ is a group of the formula Ia, Ib or Ic in which $R_5$ is hydrogen, lower alkyl, lower alk-3-yn-2-yl or lower alk-2-yn-1-yl, and $R_6$ is a group of the formula Id or Ie with $R_1$, $R_2$, $R_3$ and $R_5$ as defined above, and their pharmaceutically acceptable salts for the treatment of diseases of the rheumatoid type and for the production of pharmaceutical preparations intended for this purpose, a method for the treatment of diseases of the rheumatoid type and pharmaceutical preparations intended for this purpose, comprising a compound of the formula I or a pharmaceutically acceptable salt thereof in addition to customary pharmaceutical adjuncts.

The invention relates in particular to the use of compounds of the formula I in which $R_1$ is $C_3$–$C_7$alk-2-en-1-yl, such as allyl or methallyl, $C_3$–$C_7$alk-3-en-2-yl, such as but-3-en-2-yl, $C_3$–$C_7$alk-2-yn-1-yl, such as prop-2-yn-1-yl, or 2-halo-$C_3$–$C_7$alkyl, such as 2-bromoisobutyl, $R_2$ is hydrogen and $R_3$ is $C_1$–$C_4$alkyl, such as methyl, di-$C_1$–$C_4$alkylaminomethyl, such as dimethylaminomethyl, or halomethyl, such as bromomethyl or $R_2$ and $R_3$, independently of one another, are hydrogen or $C_1$–$C_4$alkyl, such as methyl or together are methylene, $R_4$ is a group of the formula Ia, Ib or Ic in which $R_5$ is hydrogen, $C_1$–$C_4$alkyl, such as methyl, $C_3$–$C_7$alk-2-en-1-yl, such as allyl or $C_3$–$C_7$alk-2-yn-1-yl, such as prop-2-yn-1-yl, $R_6$ is a group of the formula Id or Ie with $R_1$, $R_2$, $R_3$ and $R_5$ as defined above, and their pharmaceutically acceptable salts for the treatment of diseases of the rheumatoid type and for the production of pharmaceutical preparations intended for this purpose, a method for the treatment of diseases of the rheumatoid type and pharmaceutical preparations intended for this purpose, comprising a compound of the formula I or a pharmaceutically acceptable salt thereof in addition to customary pharmaceutical adjuncts.

The invention relates especially to the use of compounds of the formula I in which $R_1$ is $C_3$–$C_7$alk-2-en-1-yl, such as allyl or methallyl, $C_3$–$C_7$alk-2-yn-1-yl, such as prop-2-yn-1-yl, or 2-halo-$C_3$–$C_7$alkyl, such as 2-bromoisobutyl, $R_2$ and $R_3$, independently of one another, are hydrogen or $C_1$–$C_4$alkyl, such as methyl, or together are methylene, $R_4$ is a group of the formula Ia, Ib or Ic in which $R_5$ is $C_1$–$C_4$alkyl, such as methyl, $C_3$–$C_7$alk-2-en-1-yl, such as allyl, or $C_3$–$C_7$alk-2-yn-1-yl, such as prop-2-yn-1-yl, and $R_6$ is a group of the formula Id or Ie with $R_1$, $R_2$, $R_3$ and $R_5$ as defined above, and their pharmaceutically acceptable salts for the treatment of diseases of the rheumatoid type and for the production of pharmaceutical preparations intended for this purpose, a method for the treatment of diseases of the rheumatoid type and pharmaceutical preparations intended for this purpose, comprising a compound of the formula I or a pharmaceutically acceptable salt thereof in addition to customary pharmaceutical adjuncts.

The invention relates first and foremost to the use of compounds of the formula I in which $R_1$ is $C_3$–$C_7$alk-2-en-1-yl, such as allyl or methallyl, $R_2$ and $R_3$, independently of one another, are hydrogen or $C_1$–$C_4$alkyl, such as methyl, $R_4$ is a group of the formula Ia, Ib or Ic in which $R_5$ is $C_1$–$C_4$alkyl, such as methyl, or $C_3$–$C_7$alk-2-en-1-yl, such as allyl, and $R_6$ is a group of the formula Id or Ie with $R_1$, $R_2$, $R_3$ and $R_5$ as defined above, and their pharmaceutically acceptable salts for the treatment of diseases of the rheumatoid type and for the production of pharmaceutical preparations intended for this purpose, a method for the treatment of diseases of the rheumatoid type and pharmaceutical preparations intended for this purpose, comprising a compound of the formula I or a pharmaceutically acceptable salt thereof in addition to customary pharmaceutical adjuncts.

The invention relates especially to the use of
3-prop-2-ynyl-thiazolidine-2,4-dione-2-(4-methyl-3-thiosemicarbazone);
3-allylthiazolidine-2,4-dione-2-(4-allyl-3-thiosemicarbazone);
3-allylthiazolidine-2,4-dione-2-(4-methyl-3-thiosemicarbazone);
3-allylthiazolidine-2,4-dione-2-(4-propynyl-3-thiosemicarbazone);
3-methallyl-5,5-dimethylthiazolidine-2,4-dione-2-(4-allyl-3-thiosemicarbazone);
3-methallylthiazolidine-2,4-dione-2-(4-methyl-3-thiosemicarbazone);
3-allyl-5-methylthiazolidine-2,4-dione-2-(4-allyl-3-thiosemicarbazone);
3-methallyl-5-methylthiazolidine-2,4-dione-2-(4-methyl-3-thiosemicarbazone);
1,1'-dithiobis{N-methylformamide-[3-methallyl-4-oxo-5-methylthiazoldinylidene}hydrazone;
1,1'-dithiobis{N-allylformamide-[3-allyl-4-oxo-5-methylthiazolidinylidene}hydrazone;
1,1'-dithiobis{N-methylformamide-[3-methallyl-4-oxo-5,5-dimethylthiazolidinylidene}hydrazone;
1,1'-dithiobis{N-allylformamide-[3-methallyl-4-oxo-5,5-dimethylthiazolidinylidene}hydrazone and
1,1'-dithiobis{N-methylformamide-[3-allyl-4-oxo-thiazolidinylidene}hydrazone
for the treatment of diseases of the rheumatoid type or for the production of pharmaceutical preparations intended for this purpose, a method for the treatment of diseases of the rheumatoid type and pharmaceutical preparations intended for this purpose, comprising a compound of the formula I or a pharmaceutically acceptable salt thereof in addition to customary pharmaceutical adjunts.

The compounds of the formula I and their pharmaceutically acceptable salts are preferably used in the form of or for the production of pharmaceutical preparations.

The pharmaceutical preparations according to the invention, which contain the compound according to the invention or pharmaceutically acceptable salts thereof, are those for enteral, such as oral, and additionally rectal and parenteral administration to (a) warm-blooded animal(s), where the pharmacological active ingredient is present on its own or together with a pharmaceutically acceptable carrier. The daily dose of the active ingredient depends on the age and individual condition and on the manner of adminstration.

The novel pharmaceutical preparations contain, for example, from about 10% to about 80%, preferably from about 20% to about 60%, of the active ingredient. Pharmaceutical preparations according to the invention for enteral or parenteral administration are, for example, those in unit dose forms, such as sugar coated tablets, tablets, capsules or suppositories, and also ampoules. These are produced in a manner known per se, for example by means of conventional mixing, granulating, coating, dissolving or lyophilising methods. Thus, pharmaceutical preparations for oral administration can be obtained by combining the active ingredient with solid carriers, if desired granulating the mixture obtained, and processing the mixture or granules, if desired or necessary, after addition of suitable adjuncts to give tablets or sugar coated-tablet cores.

Suitable carriers are in particular fillers, such as sugars, for example lactose, sucrose, mannitol or sorbitol, cellulose preparations and/or calcium phosphates, for example tricalcium phosphate or calcium hydrogen phosphate, and also binders, such as starch pastes, using, for example, maize, wheat, rice or potato starch, gelatin, tragacanth, methylcellulose and/or polyvinylpyrrolidone, if desired, disintegrants, such as the abovementioned starches, and also carboxymethyl starch, crosslinked polyvinylpyrrolidone, agar, alginic acid or a salt thereof, such as sodium alginate. Adjuncts are primarily flow agents, flow conditioners and lubricants, for example silica, talc, stearic acid or salts thereof, such as magnesium stearate or calcium stearate, and/or polyethylene glycol. Sugar coated tablet cores are provided with suitable coatings, if desired enteric coatings, inter alia concentrated sugar solutions which may contain gum arabic, talc, polyvinylpyrrolidone, polyethylene glycol and/or titanium dioxide, coating solutions in suitable organic solvents or solvent mixtures or, for the production of enteric coatings, solutions of suitable cellulose preparations, such as acetylcellulose phthalate or hydroxypropyl methylcellulose phthalate being used. Colorants or pigments, for example for identifying or for marking various active ingredient doses, are additionally added to the tablets or sugar coated tablet coatings.

Other orally administrable pharmaceutical preparations are hard gelatin capsules and soft, sealed capsules made of gelatin and a plasticiser, such as glycerol or sorbitol. The hard gelatin capsules can contain the active ingredient in the form of granules, for example mixed with fillers, such as lactose, binders, such as starches, and/or lubricants, such as talc or magnesium stearate, and, if desired, stabilisers. In soft capsules the active ingredient is preferably dissolved or suspended in suitable liquids, such as fatty oils, liquid paraffin or liquid polyethylene glycol, it also being possible to add stabilisers.

Suitable rectally administrable pharmaceutical preparations are, for example, suppositories, which are composed of a combination of the active ingredient with a suppository base. Suitable suppository bases are, for example, natural or synthetic triglycerides, paraffin hydrocarbons, polyethylene glycol or higher alkanols. Gelatin rectal capsules which contain a combination of the active ingredient with a base substance can also be used. Possible base substances are, for example, liquid triglycerides, polyethylene glycol or paraffin hydrocarbons.

Aqueous solutions of an active ingredient in water-soluble form are primarily suitable for parenteral administration, for example a water-soluble salt, and also suspensions of the active ingredient, such as appropriate oily injection suspensions, suitable lipophilic solvents or vehicles, such as fatty oils, for example sesame oil, or synthetic fatty acid esters, for example ethyl oleate or triglycerides, being used or aqueous injection suspensions which contain viscosity-increasing substances, for example sodium carboxymethylcellulose, sorbitol and/or dextran, and if desired also stabilisers.

The dose of the active ingredient depends on the warm-blooded species, the age and individual condition and the manner of administration. In the normal case, an approximate daily dose of about 5 mg to about 1000 mg, in particular of about 10 mg to about 200 mg, is to be estimated for a patient weighing approximately 75 kg in the case of oral administration. This can be given in one dose or divided into several, for example 2 to 4, individual doses. Pharmaceutical preparations in unit dose form thus contain from about 5 mg to about 250 mg, in particular from about 10 mg to about 50 mg.

The following examples serve to illustrate the invention, but these are not intended to restrict it in any way in its area of validity.

EXAMPLE 1

Tablets, each comprising 10 mg of 3-allyl-5-methylthiazolidine-2,4-dione-2-(4-allyl-3-thiosemicarbazone) or a salt, for example the diethanolammonium salt, thereof can be prepared as follows:

Composition (10,000 tablets)

| Active ingredient | 100.0 g |
|---|---|
| Lactose | 450.0 g |
| Potato starch | 350.0 g |
| Gelatin | 10.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened with an ethanolic solution of the gelatin and granulated by means of a sieve. After drying, the remainder of the potato starch, the magnesium stearate, the talc and the silica are added and the mixture is compressed to give tablets 100.0 mg in weight and 50.0 mg active ingredient content each, which, if desired, can be provided with breaking notches for finer adjustment of the dose.

EXAMPLE 2

Hard gelatin capsules, comprising 20 mg of active ingredient, for example 3-allyl-5-methylthiazolidine-2,4-dione-2-(4-allyl-3-thiosemicarbazone) or a salt, for example the diethanolammonium salt, thereof can be prepared, for example, in the following way:

Composition (for 1000 capsules)

| Active ingredient | 20.0 g |
|---|---|
| Lactose | 240.0 g |
| Microcrystalline cellulose | 30.0 g |
| Sodium lauryl sulfate | 2.0 g |
| Magnesium stearate | 8.0 g |

The sodium lauryl sulfate is sieved into the lyophilised active ingredient by means of a sieve having a mesh width of 0.2 mm. The two components are intimately mixed. The lactose is then first sieved in by means of a sieve having a mesh width of 0.6 mm and then the microcrystalline cellulose by means of a sieve having a mesh width of 0.9 mm. After this, the mixture is again intimately mixed for 10 minutes. The magnesium stearate is finally sieved in by means of a sieve having a mesh width of 0.8 mm. After mixing for a further 3 minutes, hard gelatin capsules of size 0 are each filled with 300 mg of the formulation obtained.

EXAMPLE 3

Hard gelatin capsules, comprising 100 mg of active ingredient, for example 3-allyl-5-methylthiazolidine-2,4-dione-2-(4-allyl-3-thiosemicarbazone) or a salt, for example the diethanolammonium salt, thereof can be prepared, for example, in the following way:

Composition (for 1000 capsules)

| Active ingredient | 100.0 g |
|---|---|
| Lactose | 250.0 g |
| Microcrystalline cellulose | 30.0 g |
| Sodium lauryl sulfate | 2.0 g |
| Magnesium stearate | 8.0 g |

The sodium lauryl sulfate is sieved into the lyophilised active ingredient by means of a sieve having a mesh width of 0.2 mm. The two components are intimately mixed. The lactose is then first sieved in by means of a sieve having a mesh width of 0.6 mm and then the microcrystalline cellulose by means of sieve having a mesh width 0.9 mm. After this, the mixture is again intimately mixed for 10 minutes. Finally, the magnesium stearate is sieved in by means of a sieve having a mesh width of 0.8 mm. After further mixing for 3 minutes, hard gelatin capsules of size 0 are each filled with 390 mg of the formulation obtained.

EXAMPLE 4

Film-coated tablets, each comprising 50 mg of 3-allyl-5-methylthiazolidine-2,4-dione-2-(4-allyl-3thiosemicarbazone) or a salt, for example the diethanolammonium salt, thereof can be prepared as follows:

Composition (for 1000 film-coated tablets)

| Active ingredient | 50.0 g |
|---|---|
| Lactose | 100.0 g |
| Maize starch | 70.0 g |
| Talc | 10.0 g |
| Calcium stearate | 2.0 g |
| Hydroxypropylmethylcellulose | 2.36 g |
| Shellac | 0.64 g |
| Water | q.s. |
| Methylene chloride | q.s. |

The active ingredient, the lactose and 40 g of the maize starch are mixed, and moistened and granulated using a paste prepared from 15 g of maize starch and water (with warming). The granules are dried, and the rest of the maize starch, the talc and the calcium sterate are added and mixed with the granules. The mixture is compressed to give tablets (weight: 240 mg) and these are coated with a solution of the hydroxypropyl methylcellulose and the shellac in methylene chloride; final weight of the film-coated tablet: 283 mg.

EXAMPLE 5

A 0.2% injection or infusion solution of 3-allyl-5-methylthiazolidine-2,4-dione-2-(4-allyl-3-thiosemicarbazone) or a salt, for example the diethanolammonium salt, thereof can be prepared, for example, in the following way:

Composition (for 1000 ampoules)

| Active ingredient | 5.0 g |
|---|---|
| Sodium chloride | 22.5 g |
| Phosphate buffer pH = 7.4 | 300.0 g |
| Demineralised water to | 2500.0 ml |

The active ingredient and the sodium chloride are dissolved in 1000 ml of water and filtered through a microfilter. The filtrate is mixed with the buffer solution and made up with water to 2500 ml. To prepare unit dose forms, glass ampoules are filled with 1.0 or 2.5 ml each, and then contain 2.0 or 5.0 mg of active ingredient each.

EXAMPLE 6

1% ointment (O/W emulsion), comprising as active ingredient, for example, 3-allyl-5-methylthiazolidine-2,4-dione-2-(4-allyl-3-thiosemicarbazone) or a salt, for example the diethanolammonium salt, thereof, having the following composition:

| Active ingredient | 1.0 g |
|---|---|
| Cetyl alcohol | 3.0 g |
| Glycerol | 6.0 g |
| Methylparaben ® | 0.18 g |
| Propylparaben ® | 0.05 g |
| Arlacel ® 60 | 0.6 g |
| Tween ® 60 | 4.4 g |
| Stearic acid | 9.0 g |
| Isopropyl palmitate | 2.0 g |
| Liquid paraffin, viscous | 10.0 g |
| Demineralised water q.s. to | 100.0 g |

EXAMPLE 7

1% gel, comprising as active ingredient, for example, 3-allyl-5-methylthizolidine-2,4-dione-2-(4-allyl-3-thiosemicarbazone) or a salt, for example the diethanolammonium salt, thereof, having the following composition:

| Active ingredient | 1.0 g |
|---|---|
| Carbopol ® 934 P | 1.0 g |
| Glycerol | 3.0 g |
| Isopropanol | 25.0 g |
| Softigen ® 767 | 0.2 g |
| Demineralised water q.s. to | 100.0 g |

EXAMPLE 8

In a manner analogous to that described in the above examples 1 to 7, pharmaceutical preparations comprising another compound of the formula I, for example
3-prop-2-ynylthiazolidine-2,4-dione-2-(4-methyl-3-thiosemicarbazone);
3-allylthiazolidine-2,4-dione-2-(4-allyl-3-thiosemicarbazone);
3-allylthiazolidine-2,4-dione-2-(4-methyl-3-thiosemicarbazone);
3-allylthiazolidine-2,4-dione-2-(4-propynyl-3-thiosemicarbazone);
3-methallyl-5,5-dimethylthiazolidine-2,4-dione-2-(4-allyl-3-thiosemicarbazone);
3-methallylthiazolidine-2,4-dione-2-(4-methyl-3-thiosemicarbazone);
3-methallyl-5-methylthizolidine-2,4-dione-2-(4-methyl-3-thiosemicarbazone);
3-propylthizolidine-2,4-dione-2-(4-methyl-3-thiosemicarbazone);
1,1'-dithiobis{N-methylformamide-[3-methallyl-4-oxo-5-methylthiazolidinylidene}hydrazone;
1,1'-dithiobis{N-allylformamide-[3-methallyl-4-oxo-5-methyl-thiazolidinylidene}hydrazone;
1,1'-dithiobis{N-methylformamide-[3-methallyl-4-oxo-5,5-dimethylthiazolidinylidene}hydrazone;
1,1'-dithiobis{N-allylformamide-[3-methallyl-4-oxo-5,5-dimethylthizolidinylidene}hydrazone or
1,1'-dithiobis{N-methylformamide-[3-allyl-4-oxo-thiazolidinylidene}hydrazone
or a pharmaceutically acceptable salt thereof can also be prepared.

What is claimed is:

1. A method for the treatment of diseases of the rheumatoid type, comprising administering to a warm-blooded organism in need thereof a therapeutically effective amount of an antirheumatoid compound of the formula I

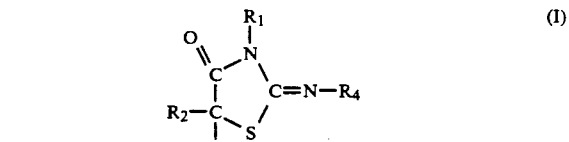

in which $R_1$ is lower alk-2-en-1-yl, lower alk-3-en-2-yl, lower alk-2-yn-1-yl or lower alkyl substituted in the 2,3-position by radicals which can be eliminated to give a double bond, $R_2$ is hydrogen and $R_3$ is methyl which is unsubstituted or substituted by radicals which can be eliminated together with hydrogen $R_2$ to give a double bond or $R_2$ and $R_3$ are both hydrogen or lower alkyl or are together methylene and $R_4$ is a group of the formula Ia, Ib or Ic

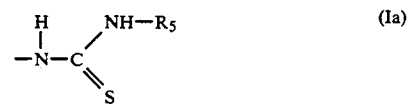

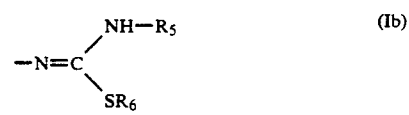

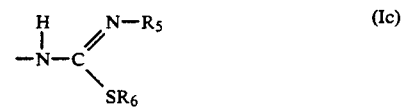

in which $R_5$ is hydrogen, lower alkyl, lower alk-2-en-1-yl or lower alk-2-yn-1-yl and $R_6$ is a group of the formula Id or Ie

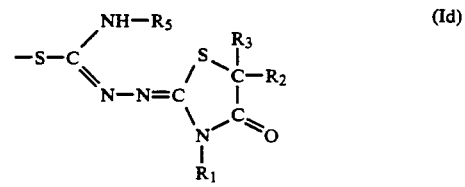

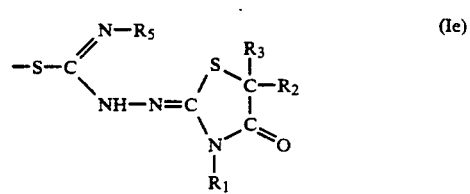

in which $R_1$, $R_2$, $R_3$ and $R_5$ are as defined, or a pharmaceutically acceptable salt thereof.

2. The method of claim 1 wherein said pharmaceutical preparation is suitable for enteral or parenteral administration.

3. The method of claim 1 wherein said pharmaceutical preparation is in unit dose form, as a tablet, capsule, suppository, injection, or infusion solution.

4. The method of claim 1 wherein said pharmaceutical preparation comprises from about 5 mg to about 250 mg of said compound or a pharmaceutically acceptable salt thereof.

5. The method of claim 1 wherein said pharmaceutical preparation comprises from about 10 mg to about 50 mg of said compound or a pharmaceutically acceptable salt thereof.

6. The method of claim 1 wherein said compound of formula I is part of a pharmaceutical preparation comprising an antirheumatoid effective amount of said compound, or a pharmaceutically acceptable salt thereof, and a pharmaceutically acceptable adjunct.

7. The method of claim 1 wherein in said compound of formula I or pharmaceutically acceptable salt thereof, $R_1$ is lower alk-2-en-1-yl, lower alk-3-en-2-yl, lower alk-2-yn-1-yl, 2- or 3-amino-, 2- or 3-lower alkylamino- or 2- or 3-di-lower alkylamino-lower alkyl, 2- or 3-lower alkyleneamino-, 2- or 3-(aza)lower alkyleneamino-, 2- or 3-(oxa)lower alkyleneamino- or 2- or 3-(thia)lower alkyleneamino-lower alkyl, 2- or 3-hydroxy-, 2- or 3-lower alkanoyloxy-, 2- or 3-lower alkoxycarbonyloxy- or 2- or 3-tri-lower alkylsilyloxy-lower alkyl or 2- or 3-halo-lower alkyl, $R_2$ is hydrogen and $R_3$ is di-lower alkylamino-lower alkyl or halomethyl or $R_2$ and $R_3$, independently of one another, are hydrogen or lower alkyl or together are methylene, $R_4$ is a group of the formula Ia, Ib or Ic in which $R_5$ is hydrogen, lower alkyl, lower alk-3-yn-2-yl or lower alk-2-yn-1-yl and $R_6$ is a group of the formula Id or Ie with $R_1$, $R_2$, $R_3$ and $R_5$ as defined above.

8. The method of claim 1 wherein in said compound of formula I or pharmaceutically acceptable salt thereof, $R_1$ is $C_3$–$C_7$alk-2-en-1-yl, $C_3$–$C_7$alk-3-en-2-yl, $C_3$–$C_7$alk-2-yn-1-yl or 2-halo-$C_3$–$C_7$alkyl, $R_2$ is hydrogen and $R_3$ is $C_1$–$C_4$alkyl, di-$C_1$–$C_4$alkylaminomethyl or halomethyl, or $R_2$ and $R_3$, independently of one another, are hydrogen or $C_1$–$C_4$alkyl or together are methylene, $R_4$ is a group of the formula Ia, Ib or Ic in which $R_5$ is hydrogen, $C_1$–$C_4$alkyl, $C_3$–$C_7$alk-2-en-1-yl or $C_3$–$C_7$alk-2-yn-1-yl, and $R_6$ is a group of the formula Id or Ie with $R_1$, $R_2$, $R_3$ and $R_5$ as defined above.

9. The method of claim 1 wherein in said compound of formula I or pharmaceutically acceptable salt thereof, $R_1$ is $C_3$–$C_7$alk-2-en-1-yl, such as allyl or methallyl, $C_3$–$C_7$alk-2-yn-1-yl, such as prop-2-yn-1-yl, or 2-halo-$C_3$–$C_7$alkyl, such as 2-bromoisobutyl, $R_2$ and $R_3$, independently of one another, are hydrogen or $C_1$–$C_4$alkyl, such as methyl, or together are methylene, $R_4$ is a group of the formula Ia, Ib or Ic in which $R_5$ is $C_1$–$C_4$alkyl, such as methyl, $C_3$–$C_7$alk-2-en-1-yl, such as allyl, or $C_3$–$C_7$alk-2-yn-1-yl, such as prop-2-yn-1-yl, and $R_6$ is a group of the formula Id or Ie with $R_1$, $R_2$, $R_3$ and $R_5$ as defined above.

10. The method of claim 1 wherein in said compound of formula I or pharmaceutically acceptable salt thereof, $R_1$ is $C_3$–$C_7$alk-2-en-1-yl, such as allyl or methallyl, $R_2$ and $R_3$, independently of one another, are hydrogen or $C_1$–$C_4$alkyl, such as methyl, $R_4$ is a group of the formula Ia, Ib or Ic in which $R_5$ is $C_1$–$C_4$alkyl, such as methyl, or $C_3$–$C_7$alk-2-en-1yl, such as allyl, and $R_6$ is a group of the formula Id or Ie with $R_1$, $R_2$, $R_3$ and $R_5$ as defined above.

11. The method of claim 1 wherein said compound of formula I is selected from the group consisting of
3-allylthiazolidine-2,4-dione-2-(4-methyl-3-thiosemicarbazone),
3-methallyl-5,5-dimethylthiazolidine-2,4-dione-2-(4-allyl-3-thiosemicarbazone),
3-methallylthiazolidine-2,4-dione-2-(4-methyl-3-thiosemicarbazone),
3-allyl-5-methylthiazolidine-2,4-dione-2-(4-allyl-3-thiosemicarbazone),
3-methallyl-5-methylthiazolidine-2,4-dione-2-(4-methyl-3-thiosemicarbazone),
3-propylthiazolidine-2,4-dione-2-(4-methyl-3-thiosemicarbazone),
3-prop-2-ynylthiazolidine-2,4-dione-2-(4-methyl-3-thiosemicarbazone),
1,1'-dithiobis{N-methylformamide-[3-methallyl-4-oxo-5-methylthiazolidinylidine}hydrazone,
1,1'-dithiobis{N-allylformamide-[3-allyl-4-oxo-5-methylthiazolidinylidene}hydrazone,
1,1'-dithiobis{N-methylformamide-[3-methallyl-4-oxo-5,5-dimethylthiazolidinylidene}hydrazone,
1,1'-dithiobis{N-allylformamide-[3-methallyl-4-oxo-5,5-dimethylthiazolidinylidene}hydrazone,
1,1'-dithiobis{N-methylformamide-[3-allyl-4-oxo-thiazolidinylidene}hydrazone,
3-allylthiazolidine-2,4-dione-2-(4-allyl-3-thiosemicarbazone), and
3-allylthiazolidine-2,4-dione-2-(4-propynyl-3-thiosemicarbazone)
or a pharmaceutically acceptable salt thereof.

* * * * *